United States Patent [19]

Lee et al.

[11] Patent Number: 5,124,483

[45] Date of Patent: Jun. 23, 1992

[54] ORTHO-ALKYLATION OF AROMATIC AMINES

[75] Inventors: Guo-shuh J. Lee, Midland, Mich.; V. Rao Durvasula, Lake Jackson, Tex.; George E. Hartwell, Midland, Mich.; Kirk D. Anderson, Brazoria, Tex.; Louis N. Moreno, Lake Jackson, Tex.; Nirad N. Shah, Lake Jackson, Tex.

[73] Assignee: The Dow Chemical Company, Midland, Mich.

[21] Appl. No.: 582,309

[22] Filed: Sep. 13, 1990

Related U.S. Application Data

[63] Continuation-in-part of Ser. No. 576,810, Aug. 6, 1990, abandoned, which is a continuation of Ser. No. 419,059, Oct. 10, 1989, abandoned.

[51] Int. Cl.$^5$ .......................................... C07C 209/68
[52] U.S. Cl. ..................... 564/409; 564/307; 564/308; 564/420; 564/430
[58] Field of Search .................. 564/409, 307, 308

[56] References Cited

U.S. PATENT DOCUMENTS

| 2,762,845 | 9/1956 | Stroh et al. | 260/578 |
|---|---|---|---|
| 2,814,646 | 11/1957 | Kolka et al. | 260/577 |
| 3,275,690 | 9/1966 | Stroh et al. | 260/576 |
| 3,649,693 | 3/1972 | Napolitano | 260/578 |
| 3,654,331 | 4/1972 | Klopfer | 260/448 R |
| 3,923,892 | 12/1975 | Klopfer | 260/578 |
| 3,952,037 | 4/1976 | Yoshitake et al. | 502/169 |
| 4,128,582 | 12/1978 | Governale et al. | 260/578 |
| 4,219,502 | 8/1980 | Ihrman et al. | 260/578 |
| 4,263,217 | 4/1981 | Malpass et al. | 502/153 |
| 4,760,185 | 7/1988 | Becker | 564/409 |

FOREIGN PATENT DOCUMENTS

| 560990 | 7/1958 | Canada . |
|---|---|---|
| 1013769 | 7/1977 | Canada . |
| 1194890 | 10/1985 | Canada . |
| 951501 | 10/1956 | Fed. Rep. of Germany . |
| 385794 | 4/1973 | Spain . |

OTHER PUBLICATIONS

Parshall et al., "Homogeneous Catalysis for Agrochemicals, Flavors and Fragrances," *Chemtech*, Jun. 1988, pp. 376–383.

Stroh et al., "Alkylation of Aromatic Amines," *Angew. Chem* 69, Jahrg. 1957, No. 4, pp. 124–131 (copy of international edition in English attached).

Grant & Hackh's Chemical Dictionary, 5th edition, "bronze", p. 97 (1987).

*Primary Examiner*—Glennon H. Hollrah
*Assistant Examiner*—Brian M. Burn

[57] ABSTRACT

Aromatic diamines, such as toluenediamine, are alkylated in the ortho position by heating the diamine in the presence of an aluminum alloy, aluminium chloride and, optionally, zinc, and then reacting with an alkene at elevated temperatures and pressures.

45 Claims, No Drawings

ORTHO-ALKYLATION OF AROMATIC AMINES

CROSS REFERENCE TO RELATED APPLICATIONS

The present application is a continuation-in-part of a co-pending application filed on or about Aug. 6, 1990, Ser. No. 576,810, now abandoned, which is a continuation of Ser. No. 419,059, filed Oct. 10, 1989, now abandoned.

BACKGROUND OF THE INVENTION

The present invention relates to a process for the alkylation of aromatic amines, particularly the ortho-alkylation of aromatic diamines.

Processes for the preparation of orthoalkylated aromatic amines from alkenes are known in the art. In one process, aluminum is dissolved in aniline to form aluminum anilide which serves as a catalyst for the alkylation of the aniline or of other aromatic amines. Such a process is taught in U.S. Pat. No. 3,649,693 to Napolitano. Napolitano teaches that the alkylation itself is conducted at significantly elevated temperatures and pressures. Various other references have taught that the addition of mercury chloride, various Friedel Crafts catalysts, iodine or iodine compounds are helpful in improving the efficiency of the reaction.

U.S. Pat. No. 4,760,185 to Becker teaches heating a diamine with an aluminum/zinc alloy and aluminum chloride in the absence of aniline until the evolution of hydrogen is complete. This catalyst mixture is then reacted with a lower alkene at significantly elevated pressure and temperature to form the alkylated phenylenediamine.

The methods known for the ortho-alkylation of aromatic diamines require substantially elevated reaction pressures and temperatures; require the presence of environmentally questionable substances such as mercury chloride; require expensive catalysts or require some combination of these factors. Thus what is needed is a method for the ortho-alkylation of aromatic amines which utilizes less expensive, less toxic catalysts and which utilizes relatively mild alkylation conditions.

SUMMARY OF THE INVENTION

The present invention involves a catalytic intermediate useful in a process for the ortho-alkylation of aromatic amines wherein the catalytic intermediate is prepared by heating an amine with (a) an aluminum alloy selected from the group consisting of aluminum/copper alloys, aluminum/magnesium alloys and aluminum/boron alloys;
(b) a Friedel Crafts catalyst;
(c) optionally, zinc; and
(d) optionally, a solvent until the evolution of hydrogen is complete.

This invention also involves a process for the orthoalkylation of aromatic amines wherein all or a portion of the catalytic intermediate prepared as described above is reacted, optionally with the addition of a second aromatic amine which may be the same as or different than the first aromatic amine, with an alkene at elevated temperature and pressure under reaction conditions sufficient to produce the ortho-alkylated aromatic amines.

The process of the present invention results in the relatively rapid formation of the ortho-alkylated aromatic amines with high yields and selectivities.

The alkylated amines prepared by the process of this invention have a variety of uses. For example, alkylated phenylenediamines prepared by the process of this invention have a broad range of uses including use as antiknock agents in gasoline; as intermediates in the dye industry and as amine extenders in reaction injection molding.

DETAILED DESCRIPTION OF THE ILLUSTRATIVE EMBODIMENTS

Aromatic amines useful in the preparation of the catalytic intermediate of this invention include those compounds having at least one aromatic ring and at least one amine substituent directly bonded to the aromatic ring or rings.

In a preferred embodiment, aromatic diamines are useful in the preparation of the catalytic intermediate of this invention. Such preferred aromatic diamines correspond to the following formulas:

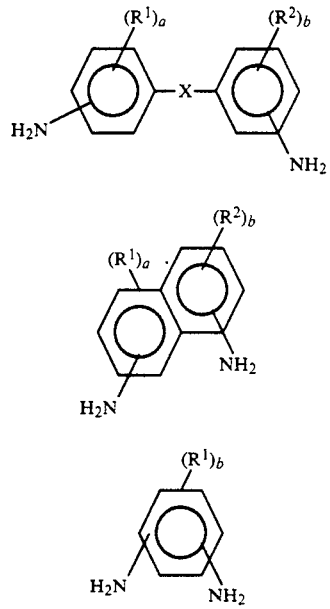

wherein X is a covalent bond, oxygen, sulfur or —CCR$^3$R$^4$)n— wherein R$^3$ and R$^4$ are separately in each occurrence hydrogen or lower alkyl and n is 1 to about 3; R$^1$ and R$^2$ are independently in each occurrence substituted or unsubstituted organic moieties such as alkyl, cycloalkyl and aralkyl moieties; and a and b are independently from zero to three. It is more preferred that R$^1$ and R$^2$ are independently in each occurrence substituted or unsubstituted C$_{1-8}$ organic moieties.

Non-limiting examples of preferred aromatic diamines useful in catalytic intermediate preparation include phenylenediamines such as m-phenylenediamine itself or substituted m-phenylenediamines. Useful substituents include C$_{1-8}$ organic moieties such as alkyl, cycloalkyl and aralkyl moieties. It is preferred that the substituents are C$_{1-3}$ alkyl groups. Non-limiting examples of substituted m-phenylenediamines useful in the catalyst preparation by the practice of this invention include 2,4-toluenediamine, 2,6-toluenediamine, 1-ethyl-2,4-phenylenediamine, 1-ethyl-2,6-phenylenediamine, 1-propyl-2,4-phenylenediamine, 1,3-dimethyl-4,6-phenylenediamine, 3,5-diethyl-2,4-toluenediamine, 3,5-diethyl-2,6-toluenediamine, 1-benzyl-2,4-phenylenediamine and mixtures thereof. The use of 2,4-toluenediamine, 2,6-toluenediamine, 3,5-diethyl-2,4-toluenediamine, 3,5-diethyl-2,6-toluenediamine and mixtures thereof is more preferred in the catalytic intermediate preparation process.

Aromatic monoamines such as aniline are also useful in the preparation of the catalytic intermediate of the present invention.

Aluminum/copper alloys useful in the preparation of the catalystic intermediate useful in the practice of the present invention are preferably those having a copper content of about 0.5 weight percent to about 30 weight percent and a corresponding aluminum content of about 99.5 weight percent to about 70 weight percent. It is more preferred that the copper content is about 2 weight percent to about 10 weight percent. It is preferred to use aluminum/copper alloys commercially available such as Aluminum 2014, 2024, 2036 and 2219. As will be recognized by those skilled in the art, in addition to aluminum and copper, aluminum/copper alloys may contain small amounts of various other metals such as silicon and magnesium.

Aluminum/boron alloys useful in the preparation of the catalytic intermediate useful in the practice of the present invention are preferably those having a boron content of about 0.5 weight percent to about 30 weight percent and a corresponding aluminum content of about 99.5 weight percent to about 70 weight percent. It is preferred that the boron content is about 2 weight percent to about 10 weight percent. Aluminum/boron alloys are commercially available and the use of the commercially available alloys is preferred. As will be recognized by those skilled in the art, in addition to aluminum and boron, aluminum/boron alloys may contain small amounts of various other metals.

Aluminum/magnesium alloys useful in the preparation of the catalytic intermediate useful in the practice of the present invention are preferably those having a magnesium content of about 0.5 weight percent to about 30 weight percent and a corresponding aluminum content of about 99.5 weight percent to about 70 weight percent. It is preferred that the magnesium content is about 2 weight percent to about 10 weight percent. It is preferred to use commercially available aluminum/magnesium alloys such as Aluminum 5083, 5182, 5252, 6009, 6010, 6061, 6063 and 6201. As is recognized by those skilled in the art, aluminum/magnesium alloys may contain small amounts of various other metals such as silicon, copper and manganese.

A Friedel Crafts catalyst, preferably aluminum chloride, is used in the preparation of the catalytic intermediate of the present invention. In addition to aluminum chloride, $SnCl_4$, $SiCl_4$, $ZrI_4$, $FeCl_3$ and $BCl_3$ are useful in the practice of this invention. The use of aluminum chloride is preferred. The use of other salts, such as zinc chloride, is not preferred in the practice of the present invention.

The amount of aluminum chloride or other salt used in the preparation of the catalytic intermediate is that amount which will result in the formation of a catalytic intermediate which will result in the production of the desired alkylated amine. When aluminum chloride is used, the amount is preferably that amount of aluminum chloride which will result in a ratio of chlorine to aluminum atoms being in the range of about 3:1 to about 1:5; preferably about 2:1 to about 1:2; and most preferably about 1:1.

Zinc is preferably used in the formation of the catalytic intermediate in the practice of this invention. Various forms of zinc are useful such as metallic zinc powder and dialkyl zinc. Any size of zinc particle which will function in the formation of the catalytic intermediate of this invention is useful. It is preferred that particle size not be too small due to problems associated with handling zinc dust. It is also preferred that particle size not be too large due to the very slow catalytic intermediate formation observed using large particles. It is preferred that the zinc be used in a mesh (U.S. Standard) size of at least about 20 and no greater than about 200. It is more preferred that the particles have a size range of from about 50 to about 150, even more preferably from about 75 to about 125 mesh, U.S. Standard.

The catalytic intermediate preparation of the present invention may be conducted neat or a solvent may be used. In some instances, a solvent/reactant may be used. In other instances, a solvent which is inert to the reaction may be used.

For purposes of the present invention, a solvent/reactant is a liquid aromatic amine capable of forming a catalytic intermediate system with aluminum, which also acts as a solvent. For example, in one embodiment of the present invention, the aromatic amine used in the preparation of the catalytic intermediate comprises diethyltoluenediamine which is a liquid in which at least some the various components used in catalytic intermediate preparation are soluble and thus acts as a solvent. Without wishing to be bound by any theory, it is believed that a portion of the diethyltoluenediamine present also appears to interact in some manner with the aluminum and other metals present to form the catalytic intermediate system which is itself soluble in the diethyltoluenediamine. The phrase "catalytic intermediate system" is used to describe the catalytic species that forms from the aromatic amine, aluminum and such other metals as may optionally be present. Non-limiting examples of solvent/reactants useful in the preparation of the catalysts of this invention include diethyltoluenediamine and aniline, including substituted anilines.

Inert solvents useful in the process of this invention are those solvents having good solubility for the catalyst system as described above, aluminum chloride and aromatic amines and also having good chemical and thermal stability. Such solvents include aromatic ether solvents which may be exemplified by phenoxy biphenyl and diphenyl ether; and alkyl polyaromatic solvents which may be exemplified terphenyl and diisopropylbiphenyl.

The catalytic intermediate is preferably formed by mixing an amine and solvent in a ratio ranging from about 1:9 to about 9:1 of amine to solvent by weight. It is more preferred that the amine to solvent ratio is greater than about 1:1. Alternatively, the amine is used without a solvent or a solvent/reactant is used. The aluminum alloy is preferably used in an amount such that there are at least about 1 part and no greater than about 10 parts of aluminum alloy per 100 parts of the amine. It is more preferred that there are about 2 to about 6 parts by weight of aluminum alloy per 100 parts by weight of diamine. The zinc, when used, is preferably used in an amount to provide at least about 0.05 and no greater than about 10 parts zinc by weight per 100 parts of amine. It is more preferred that there is about 0.1 to about 2.5 parts by weight of zinc per 100 parts by weight of amine. Aluminum chloride is preferably used in an amount to provide a chlorine to aluminum atom ratio of about 1:1.

The slurry resulting from the above mixture is heated with the evolution of hydrogen until the metals have dissolved. The completion of catalytic intermediate formation is indicated by the cessation of hydrogen evolution. After venting the hydrogen, the resulting catalytic intermediate is used in the alkylation process in an amount sufficient to provide preferably at least about 1 and no greater than about 10 weight percent metals based on the weight of the amine to be alkylated. Metals in this context refer to either the aluminum alloy or the mixture of aluminum alloy and zinc metals. It is preferred to use sufficient catalytic intermediate to provide at least about 2 and no greater than about 6 weight percent metals.

The alkylation process of the present invention is useful in the ortho-alkylation of the amine used in the catalytic intermediate preparation and in the ortho-alkylation of amines differing from the amine used in the catalyst preparation. In the former situation, catalytic intermediate preparation and alkylation may take place in a single reactor without isolation of the catalytic intermediate itself, although separate reactors may be used. In the latter situation, the catalytic intermediate is prepared in one step and may be stored or transported as necessary and then used in a separate alkylation process. For example, toluenediamine may be used in the preparation of the catalytic intermediate and also be the aromatic amine which is alkylated. In contrast, diethyltoluenediamine may be used in the catalytic intermediate preparation and toluenediamine used as the aromatic amine to be alkylated.

As discussed above, the aromatic amine to be alkylated may be the same amine used in the preparation of the catalytic intermediate or may be a different amine. The aromatic amines which may be alkylated by the process of this invention are the same as those used in catalytic intermediate preparation with the exception that the amines to be alkylated are not substituted in the positions ortho to the amine group(s). In a preferred embodiment, toluenediamine is ortho-alkylated to form diethyltoluenediamine.

The alkenes useful in this invention are alkenes containing from two to about eighteen carbon atoms. The alkenes may be unsubstituted or may contain inert substituents and may contain single or multiple unsaturations. It is preferred that the alkenes contain from about two to about twelve carbon atoms and more preferred that they contain from about two to about six carbon atoms. It is most preferred to use alkenes containing from two to about four carbon atoms. Non-limiting examples of alkenes useful in the alkylation reaction of this invention include ethene, propene and butene. It is particularly preferred to use ethene.

One skilled in the art will recognize that both the alkylation reaction and the catalytic intermediate preparation and their combination may be conducted in a batch or continuous manner. As discussed above, the catalytic intermediate preparation may be conducted separately from the alkylation reaction in that the catalytic intermediate is prepared and then stored and/or transported prior to being used in the alkylation reaction. Alternatively, the catalyst may be prepared, but not isolated or collected prior to being used in the alkylation reaction. Those skilled in the art will recognize that choice of reactors will depend in part on whether the catalytic intermediate preparation and alkylation reactions take place in the same reactor. The reactor in which the catalytic intermediate is prepared must be designed to withstand hydrogen production and should be free of metals known to be detrimental to the formation of the catalytic intermediate system. An example of such a reactor is a glass-lined reactor. The reactor used in the alkylation process should be inert and capable of withstanding elevated pressures and temperatures. Examples of reactors useful in the alkylation process include those constructed of carbon steel, titanium and zirconium. Clearly, those processes in which the catalytic intermediate is prepared and the alkylation reaction occurs in the same reactor will require a reactor which meets the criteria of both.

The choice of conditions useful in the alkylation reaction of the present invention will depend, in part, on the choice of alkene used as an alkylating agent. For example, one skilled in the art will recognize that alkylation pressures and temperatures will vary depending on the alkylating agent. One skilled in the art will also recognize that the choice of other reaction parameters, whether the alkylation reaction should be done in a batch or a continuous manner and similar decisions will be made based on the particular requirements of a given process. It will also be recognized that one skilled in the art understands the dangers of working at high pressures and that selections of temperatures and pressures will be made in accordance with safe engineering practices.

In a preferred embodiment of this invention wherein the alkene used is ethene, preferred temperatures for the alkylation process are at least about 250° C. and no greater than about 350° C. It is more preferred that the ethylation process be conducted at temperatures of at least about 270° C. and no greater than about 330° C. Ethene pressures preferred in alkylation process range from at least about 250 psig up to about 3000 psig. Due to the expense of operating high pressure equipment, lower pressures are often preferred for commercial reasons. In a particularly preferred embodiment, the ethylation step is conducted at pressures of at least about 250 psig to no greater than about 1500 psig, more preferably no greater than about 1000 psig, and most preferably no greater than about 700 psig.

The following illustrative examples are provided only to illustrate the invention and should not be interpreted as limiting it in any way. Unless stated otherwise, all parts and percentages are by weight.

EXAMPLE 1

Preparation of Diethyltoluenediamine

A 150-g portion of 2,4-toluenediamine is heated with 5 g of an aluminum/copper alloy containing about 4.4 percent copper and 7.5 g of aluminum chloride to 200° C. with stirring in a 600 cubic centimeter Hastelloy* C Parr (Hastelloy is a trademark of the Cabot Corporation) reactor with a glass liner with a mechanical stirrer. Hydrogen begins to evolve at about 175° C. and is complete after about 90 minutes. After venting the hydrogen, the reaction mixture is then reacted with ethene in a stirred (1500 rpm) autoclave at a temperature of 290° to 300° C. and an ethene pressure of 1000 psig. The alkylation is complete after two hours and the yield of diethyltoluenediamine is 96 percent based on the toluenediamine reacted as determined by gas chromatography.

EXAMPLE 2

The general procedure outlined in Example 1 is followed. A mixture of 2,4-toluenediamine and 2,6-toluenediamine in a weight ratio of about 80:20 is heated with 3.0 g of aluminum/copper alloy containing about 6.3 percent copper and 4.5 g of aluminum chloride. In Run 1, no zinc powder is added with the aluminum/copper alloy and in Run 2, 1.0 g of zinc powder (100 mesh, U.S. Standard) is added with the aluminum/copper alloy. In each case, the reaction is allowed to proceed for one hour. The results obtained are shown in Table I below.

TABLE I

| Run | Zinc Powder (g) | % Yield of Diethyltoluenediamine |
|---|---|---|
| 1 | 0 | 8 |
| 2 | 1 | 96 |

A comparison of Examples 1 and 2 demonstrates that the addition of zinc to the catalyst preparation results in an alkylation process which gives comparable yields of diethyltoluenediamine in substantially less time and with lower catalyst dosage than those obtained in the absence of the zinc powder.

EXAMPLE 3

In the following examples, 50 g toluenediamine, 25 g diethylaniline solvent and the amounts of aluminum alloy and aluminum chloride specified in Table II below, are charged to a 300 ml stainless steel Parr reactor which is flushed with nitrogen. In Runs 1-4, the aluminum/boron alloy used contains about five percent boron. In Runs 5 and 6, the aluminum/copper alloy used contains about six percent copper. In Runs 3 and 4, a glass-lined reactor is used. In the remaining runs, an unlined reactor is used. Also in Run 4, zinc powder (100 mesh, U.S. Standard) is added in the amount specified. The system is closed and heated to about 200° C. for about one hour with stirring. The stirring is stopped and the generated hydrogen is vented. The reactor is flushed with nitrogen and then charged with ethene to maintain the pressure specified in the table below. Stirring is resumed and the reactor is heated to 300° C. and maintained at this temperature. The pressure is varied in some of the runs as indicated in the table below. The uptake of ethene is noted and heating is stopped at the time specified in the table below. Ethene is vented out when the reactants are hot. The reactants are cooled to room temperature and the reaction mixture is analyzed by gas chromatography. The results obtained are shown in Table II below.

TABLE II

| Run | Catalyst | Weight of Catalyst (g) | Solvent | Pressure | Time | Conversion | % Yield DETDA |
|---|---|---|---|---|---|---|---|
| 1 | Al—B/AlCl$_3$ | 0.7/1.7 | No | 1000 | 90 | 65 | 24.3 |
| 2 | Al—B/AlCl$_3$ | 0.7/1.7 | DEA | 1000 | 240 | 73.8 | 29.1 |
| 3 | Al—B/AlCl$_3$ | 1.4/3.4 | DEA | 700 | 150 | 97.8 | 73.7 |
| 4 | Al—B/Zn/AlCl$_3$ | 1.4/1.0/3.4 | DEA | 1000 | 15 | 99.6 | 93.5 |
| 5 | Al—Cu/AlCl$_3$ | 1.6/3.4 | DEA | 1000 | 120 | 78.2 | 30.1 |
| 6 | Al—Cu/AlCl$_3$ | 0.8/1.7 | DEA | 1000 | 270 | 78.5 | 32.4 |

The data in Table II above demonstrate the effectiveness of the present invention.

What is claimed is:

1. A process for the ortho-alkylation of aromatic diamines wherein:
   (1) a catalytic intermediate is prepared by heating the diamine with,
      (a) an aluminum alloy selected from the group consisting of aluminum/copper alloys having a copper content of about 0.5 weight percent to about 30 weight percent, aluminum/magnesium alloys and aluminum/boron alloys;
      (b) a Friedel Crafts catalyst;
      (c) optionally, zinc; and
      (d) optionally, a solvent
   until the evolution of hydrogen is complete; and
   (2) a portion of the catalytic intermediate prepared in step (1) is reacted with alkene at elevated temperature and pressure under reaction conditions sufficient to produce the ortho-alkylated aromatic diamines.

2. The process of claim 1 wherein the aromatic amine is an m-phenylenediamine containing at least one $C_{1-8}$ organic substituent selected from the group consisting of $C_{1-8}$ alkyl, cycloalkyl and aralkyl moieties.

3. The process of claim 2 wherein the organic substituent is selected from the group consisting of $C_{1-3}$ alkyl moieties.

4. The process of claim 3 wherein the diamine is selected from the group consisting of 2,4-toluenediamine, 2,6-toluenediamine and mixtures thereof.

5. The process of claim 1 wherein the aluminum alloy is an aluminum/copper alloy having a copper content of about 0.5 weight percent to about 30 weight percent.

6. The process of claim 1 wherein the aluminum alloy is an aluminum/boron alloy.

7. The process of claim 1 wherein the aluminum alloy is an aluminum/magnesium alloy.

8. The process of claim 1 wherein the alkene is selected from the group consisting of ethene, propene and butene.

9. The process of claim 8 wherein the alkene is ethane.

10. The process of claim 1 wherein the aluminum alloy in step (1) is used in an amount to provide at least about 1 and no greater than about 10 weight percent based on the weight of the aromatic diamine.

11. The process of claim 1 wherein the aluminum alloy in step (1) is used in an amount to provide at least about 2 and no greater than about 3 weight percent based on the weight of the aromatic diamine.

12. The process of claim 1 wherein zinc is used in an amount of at least about 0.05 weight percent and no greater than about 10 weight percent based on the weight of the aromatic diamine.

13. The process of claim 1 wherein the amount of zinc used is at least about 0.1 weight percent and no greater than about 2.5 weight percent based on the weight of the aromatic diamine.

14. The process of claim 1 wherein a solvent is used.

15. The process of claim 14 wherein the solvent is an aromatic ether.

16. The process of claim 14 wherein the solvent is an alkyl polyaromatic solvent.

17. The process of claim 1 wherein zinc is used and a solvent is used.

18. The process of claim 17 wherein step (2) is conducted at a pressure of at least about 250 psi and no greater than about 1000 psi.

19. The process of claim 18 wherein step (2) is conducted at a pressure of at least about 250 psi and no greater than about 700 psi.

20. The process of claim 17 wherein the aluminum alloy is an aluminum/copper alloy.

21. The process of claim 17 wherein the aluminum alloy is an aluminum/boron alloy.

22. The process of claim 17 wherein the aluminum alloy is an aluminum/magnesium alloy.

23. The process of claim 1 wherein the Freidel Crafts catalyst is aluminum chloride.

24. The process of claim 1 wherein step (1) is conducted in a glass-lined reactor.

25. The process of claim 1 wherein zinc is used and step (1) and step (2) are conducted in a glass-lined reactor.

26. The process of claim 24 wherein step (2) is conducted in a zirconium reactor.

27. The process of claim 24 wherein step (2) is conducted in a titanium reactor.

28. The process of claim 24 wherein step (2) is conducted in a carbon steel reactor.

29. The process of claim 25 wherein step (2) is conducted in a zirconium reactor.

30. The process of claim 25 wherein step (2) is conducted in a titanium reactor.

31. The process of claim 2 wherein zinc is used and a solvent is used.

32. The process of claim 31 wherein the aromatic diamine is selected from the group consisting of 2,4-toluenediamine, 2,6-toluenediamine and mixtures there of and step (2) is conducted at a pressure of at least about 250 psi and no greater than about 1000 psi.

33. The process of claim 32 wherein zinc is used, a solvent is used and step (2) is conducted at a pressure of at least about 250 psi and no greater than about 700 psi.

34. A process for the preparation of ortho-alkylated amines comprising preparing a catalytic intermediate by heating a first aromatic amine with
  (1) an aluminum alloy selected from the group consisting of aluminum/copper alloys having a copper content of about 0.5 weight percent to about 30 weight percent, aluminum/magnesium alloys and aluminum/boron alloys;
  (2) aluminum chloride;
  (3) optionally, zinc, having a particle size in the range of from about 20 to 200 mesh, U.S. Standard; and
  (4) optionally, a solvent
and subsequently reacting the catalytic intermediate with an alkene and, optionally, a second aromatic amine at elevated temperature and pressure under reaction conditions sufficient to produce the ortho-alkylated aromatic amines.

35. The process of claim 34 wherein the first aromatic amine and the second aromatic amine are phenylenediamines.

36. The process of claim 35 wherein the phenylenediamines are selected from the group consisting of toluenediamine, diethyltoluenediamine and mixtures thereof.

37. The process of claim 34 wherein the first aromatic amine and the second aromatic amine are the same.

38. The process of claim 34 wherein the first aromatic amine and the second aromatic are different.

39. The process of claim 34 wherein the alkene is selected from the group consisting of ethene, propene, butene and mixtures thereof.

40. The process of claim 37 wherein the alkene is ethene.

41. The process of claim 34 wherein the preparation of the catalytic intermediate and the reaction of the alkene with the catalyst are carried out in the same reactor.

42. The process of claim 34 wherein the preparation of the catalytic intermediate and the reaction of the alkene with the catalyst is carried out in different reactors.

43. A process for the preparation of diethyltoluenediamine comprising preparing a catalytic intermediate by heating a first aromatic amine selected from the group consisting of toluenediamine, diethyltoluenediamine and mixtures thereof with
  (1) an aluminum alloy selected from the group consisting of aluminum/copper alloys, aluminum/boron alloys and aluminum/magnesium alloys;
  (2) aluminum chloride;
  (3) zinc, having a particle size in the range of from about 20 to 200 mesh, U.S. Standard; and
  (4) optionally, a solvent
and subsequently reacting the catalytic intermediate with ethene and, optionally, additional toluenediamine with the proviso that if the first aromatic amine is diethyltoluenediamine, toluenediamine will be added at this step, at elevated temperature and pressure under reaction conditions sufficient to produce the diethyltoluenediamine.

44. A process for the ortho-alkylation of aromatic diamines wherein:
  (1) a catalytic intermediate is prepared by heating the diamine with
    (a) an aluminum alloy selected from the group consisting of aluminum/copper alloys, aluminum/magnesium alloys and aluminum/boron alloys;
    (b) a Friedel Crafts catalyst;
    (c) zinc; and (d) optionally, a solvent
  until the evolution of hydrogen is complete; and
  (2) a portion of the catalytic intermediate prepared in step (1) is reacted with an alkene at elevated temperature and pressure under reaction conditions sufficient to produce the ortho-alkylated aromatic diamines.

45. The process of claim 42 wherein the catalytic intermediate is prepared in a glass lined reactor and the reaction of the alkene with the catalytic intermediate is carried out in a carbon steel reactor.

* * * * *